United States Patent [19]

Kuo et al.

[11] Patent Number: 4,474,758

[45] Date of Patent: Oct. 2, 1984

[54] HAEMOPHILUS INFLUENZAE TYPE B AND PERTUSSIS OUTER MEMBRANE COMPONENT COMBINED VACCINE

[75] Inventors: Joseph S. C. Kuo, Orangeburg; Nobuo Monji, Palisades, both of N.Y.

[73] Assignee: American Cyanamid Company, Stamford, Conn.

[21] Appl. No.: 323,523

[22] Filed: Nov. 19, 1981

[51] Int. Cl.³ .................. A61K 39/10; A61K 39/102
[52] U.S. Cl. ........................................ 424/92; 424/88
[58] Field of Search ................................. 424/88, 92

[56] References Cited

U.S. PATENT DOCUMENTS

| | | | |
|---|---|---|---|
| 3,395,219 | 7/1968 | Millman | 424/92 |
| 3,465,078 | 9/1969 | Spiesel | 424/92 |
| 4,196,192 | 4/1980 | Kuo | 424/92 |
| 4,220,717 | 9/1980 | Kuo | 424/92 |

OTHER PUBLICATIONS

King, S., et al., Lancet, Oct. 3, 1981, (2)8249, pp. 705–709.

*Primary Examiner*—Blondel Hazel
*Attorney, Agent, or Firm*—C. F. Costello, Jr.

[57] ABSTRACT

A combined vaccine for eliciting polyribosyl ribitol phosphate (PRP) antibody formations in warm-blooded animals has been invented. The combined vaccine comprises the capsular polysaccharide PRP isolated and purified from *Haemophilus influenzae* type b and antigens isolated and purified from an outer membrane component of *Bordetella pertussis*.

A method for inducing active immunization in warm-blooded animals against systemic infection caused by the pathogen *H. influenzae* type b has also been invented. The method comprises administering an immunogenic amount of a combined vaccine comprising the capsular polysaccharide PRP isolated and purified from *H. influenzae* type b and antigens isolated and purified from an outer membrane component of *B. pertussis*.

7 Claims, 4 Drawing Figures

HAEMOPHILUS INFLUENZAE TYPE B AND PERTUSSIS OUTER MEMBRANE COMPONENT COMBINED VACCINE

BACKGROUND OF THE INVENTION

1. Field of the Invention

This invention relates to a combined vaccine for eliciting polyribosyl ribitol phosphate (PRP) antibody formations in warm-blooded animals. This invention also relates to a method for inducing active immunization in warm-blooded animals against systemic infection caused by the pathogen *H. influenzae* type b.

2. Prior Art Statement

The applicants are not aware of any prior art which in their respective judgments, as a person skilled in the vaccine art, anticipates or renders obvious the subject matter of this invention. However, to develop the background and establish the state of the prior art, the following references are set forth:

(a) Kuo, J. S.-C. "Combined *HAEMOPHILUS INFLUENZAE* Type B and Pertussis Vaccine", U.S. Pat. No. 4,196,192 issued Apr. 1, 1980, and Kong, A. S. and Morse, S. I. "The Effect of *BORDETELLA PERTUSSIS* On The Antibody Response In Mice to Type III Pneumococcal Polysaccharide", Journal of Immunology 116 989–993 (1976). These references disclose the use of *B. pertussis* whole cells to enhance the antigenicity of an *H. influenzae* and a pneumococcal polysaccharide, respectively; and (b) Robbins, J. B., Horton, R. E., and Kranse, R. M. "New Approaches For Inducing Natural Immunity To Pyogenic Organisms" Proceedings of a Symposium Mar. 21–23, 1973, DHEW Publication No. (NIH) 74-553. This reference states on page 164 that no noticable adjuvant effect is reported with an endotoxin used in conjunction with a pneumococcus polysaccharide and possibly with other polysaccharides.

SUMMARY OF THE INVENTION

A combined vaccine for eliciting PRP antibody formations in warm-blooded animals has been invented. The combined vaccine comprises the capsular polysaccharide PRP isolated and purified from *H. influenzae* type b and antigens isolated and purified from an outer membrane component of *B. pertussis*.

Other embodiments are wherein said polyribosyl ribitol phosphate is obtained from *H. influenzae* type b Rab strain; and wherein said *B. pertussis* antigens are obtained from *B. pertussis* strain 138. Another embodiment is wherein said warm-blooded animal is a human child.

A method for inducing active immunization in warm-blooded animals against systemic infection caused by the pathogen *H. influenzae* type b has also been invented. The method comprises administering an immunogenic amount of a combined vaccine comprising the capsular polysaccharide PRP isolated and purified from *H. influenzae* type b and antigens isolated and purified from at least one *B. pertussis* outer membrane component. Another embodiment is wherein said systemic infection is meningitis.

DETAILED DESCRIPTION

The isolation and purification of *H. influenzae* type b polyribosyl ribitol phosphate (PRP) is described by Kuo, J. S.-C. "Isolation and Purification of Polyribosyl Ribitol Phosphate from *Haemophilus Influenzae* Type B" in U.S. Pat. No. 4,220,717 issued Sept. 2, 1980 which is incorporated by reference.

*B. pertussis* (strain 138) cells are grown on Bordet-Gengou medium, subcultured once at 37° C., and then used to inculate a Cohen and Wheeler (herein C.W.) medium. The growth and incubation is similar to that disclosed by S. M. Cohen and M. W. Wheeler in the American Journal of Public Health 36, 371–376 (1946) which is incorporated by reference. The organisms are grown in the C.W. broth (40 ml) as a seed cultured for a 400 ml. fermentation.

Four hundred liter fermentation is then carried out using the C.W. liquid culture medium. After 24 hrs. growth, the organisms are harvested by centrifugation, suspended in phosphate buffered saline (0.1M, pH 7.0) and inactivated by 0.015% thimerosal.

Outer membrane components are isolated from the cells by a lysozyme treatment method and by a lithium chloride-lithium acetate (herein LiCl-LiAc) method.

LYSOZYME TREATMENT METHOD

*B. pertussis* cells (1.1 g wet weight) are suspended in 16 ml of ice cold distilled water. The following reagents are then added: (a) 11 ml of 2M sucrose; (b) 10 ml of 0.1M [tris (hydroxymethyl)aminomethane]·HCL, which is abbreviated herein as "tris·HCL" (pH 7.8 at 4° C.); (c) 0.2 ml of 1% NaEDTA (pH 7.0); and (d) 1.8 ml of 1.0% lysozyme.

The mixture is warmed to 30° C. and then kept at that temperature for 60 minutes. After 30 minutes incubation, 400 μg of deoxyribonuclease is added to decrease the viscosity of the solution.

The suspension is centrifuged at 20,000xg (13,000 rpm) for 60 minutes at 30° C. to remove the spheroplast. The outer membrane in the supernatant is precipitated by adjusting the pH to 5.0 with dilute HCL (0.2N) and centrifuged at 35,000xg (17,000 rpm) for 15 minutes. The precipitated outer membrane is washed twice with ice cold distilled water and stored at −20° C.

Figure 1:
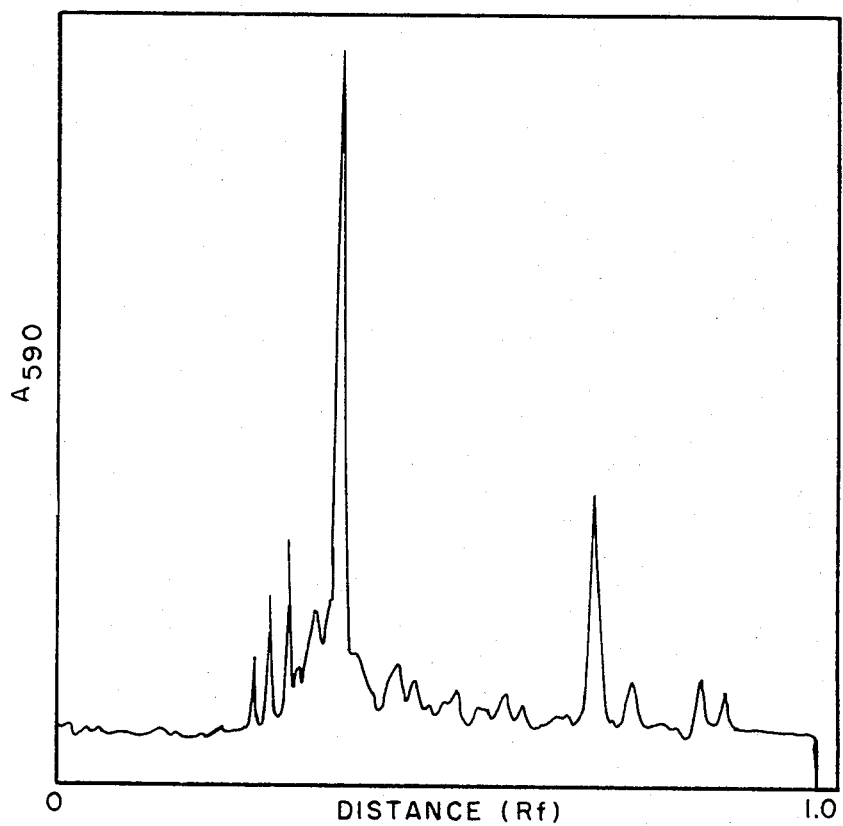
FIG. 1 describes SDS-PAGE protein profile of an outer membrane component isolated by a lysozyme treatment method after staining with coomassie brilliant blue R-250.

A profile of the outer membrane components in SDS (sodium dodecyl sulfate)-PAGE (polyacrylamide gel electrophoresis) obtained by this treatment is described in FIG. 1. The SDS-PAGE is done in a 10 cm 10% acrylamide gel containing 0.33M tris·HCL buffer (pH 8.8) and 0.1% SDS. Prior to application, the sample is solubilized in the buffer containing 0.0625M tris·HCL, pH 6.8, 2% SDS, 10% glycerol and 5% 2-mercaptoethanol.

LiCl-LiAc Method

This isolation method is similar to that described by McDade, R. L. and Johnston, K. H. "Characterization of Serologically Dominant Outer Membrane Proteins of *Neisseria Gonorrhoeae*" in the Journal of Bacteriology 141 1183-1191 (1980) which is incorporated by reference.

Two gm wet weight of *B. pertussis* cells are washed twice with 20 ml of distilled water and suspended in 40 ml of 200 mM LiCl and 100 mM of LiAc (pH 6.0, herein LCA buffer). The suspension is shaken rigorously in the presence of 6 mm glass beads at 45° C. for 2 hrs. (160 oscillations/min.). The resulting mixture is then transferred to a centrifuge and the beads washed once with 0.5 ml of LCA buffer. The wash is added to the centrifuge. The mixture is then centrifuged at 10,000 rpm (12,000xg) for 15 min. at 4° C. The supernatant is collected and centrifuged again at 14,500 rpm (25,000xg) at 4° C.

The collected supernatant is then applied to 5.0×60 cm sepharose 6B Cl column pre-equilibrated with 10 mM tris·HCl buffer, pH 8.0, with 200 mM NaCl and with 0.02% (wt/v) sodium azide (herein TS buffer).

The column is eluted with the TS buffer. The absorbance of each fraction is measured at 280 nm. The fractions of each peak are pooled and concentrated to 1 mg protein/ml.

Figure 2:
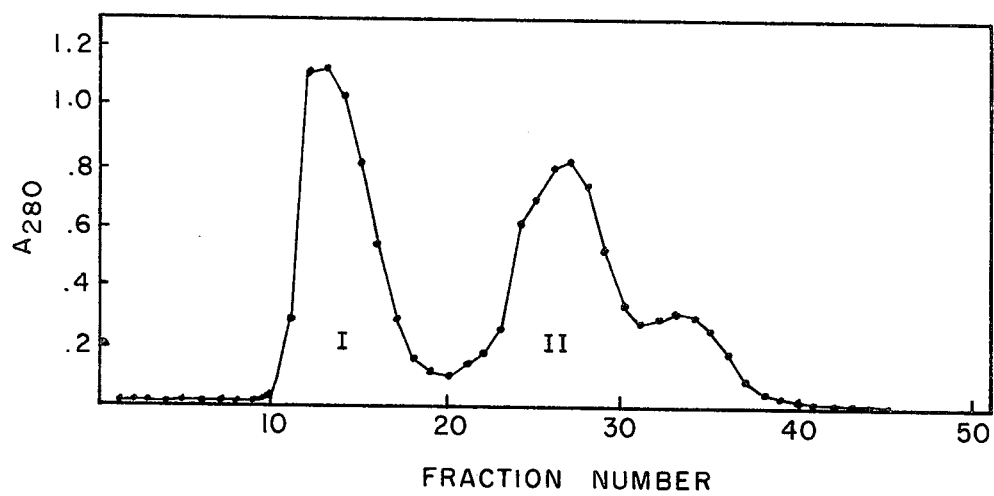
FIG. 2 describes Sepharose 6B Cl chromatographic profile of an outer membrane component isolated by a LiCl-LiAc method as measured at 280 nm wavelength.
Figure 3:
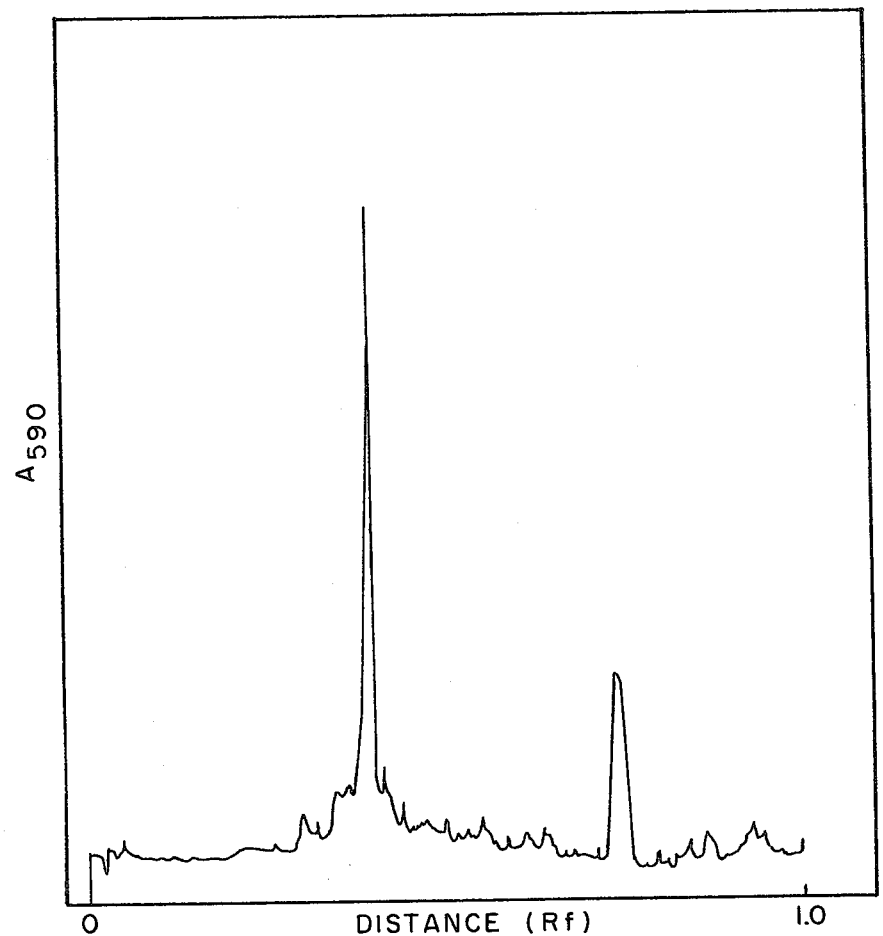
FIG. 3 describes SDS-PAGE protein profile of outer membrane component I of FIG. 2 isolated by an LiCl-LiAc method, followed by sepharose 6B CL chromatography.
Figure 4:
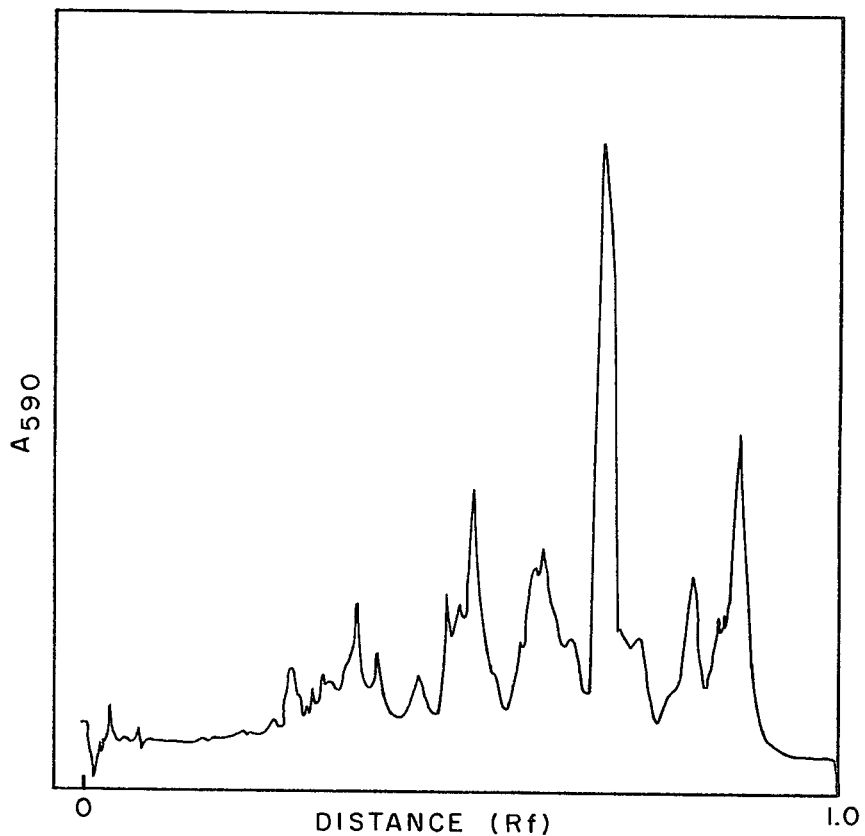
FIG. 4 describes SDS-PAGE protein profile of outer membrane component II of FIG. 2 isolated by an LiCl-LiAc method, followed by sepharose 6B CL chromatography.

A sepharose 6B CL column chromatography profile of the outer membrane components obtained by this treatment is described in FIG. 2. A protein profile in SDS-PAGE of the component peaks I and II shown in FIG. 2 is further described in FIGS. 3 and 4, respectively.

The starting materials for the preparation of the vaccine of this invention is purified *H. influenzae* b PRP and at least one purified outer membrane protein isolated from *B. pertussis*. The term outer membrane is intended to be generic and includes one or more of those membranes which are external to the cytoplasmic membrane. That is, the term outer membrane excludes the cytoplasmic membrane.

To prepare a PRP vaccine, lyophilized PRP is dissolved in phosphate buffered saline (PBS) at pH 7.0. The PRP solution is sterilized by membrane filtration through an 0.22μ Millipore filter. The sterile vaccine is stored at 4° C. until needed.

A PRP-*B. pertussis* outer membrane component combined vaccine is prepared by combining PRP with various concentrations of at least one purified outer membrane component dissolved in an appropriate buffer.

EXAMPLE 1

A 0.3 ml PRP solution (1 mg/ml PBS) and 3.6 ml (830 μg protein/ml PBS) of *B. pertussis* outer membrane prepared by lysozyme treatment method are added to 11.1 ml of PBS containing 0.01% thimerosal to make a vaccine solution containing 10 μg PRP and 100 μg protein per dose (0.5 ml).

The combined vaccine (0.5 ml per dose) is then injected into young rats; they are injected once a week for three weeks. The age and the strain of each rat is similar.

The results of the antibody response to vaccines 1 and 2 prepared at two different times by the above procedure are as follows:

| | | PRP ANTIBODY LEVEL (ng/ml) | |
|---|---|---|---|
| Rat # | Vaccine 1 | Rat # | Vaccine 2 |
| 1 | 56 | 5 | 80 |
| 2 | 266 | 6 | 596 |
| 3 | 70 | 7 | 542 |
| 4 | 10 | 8 | 500 |

Sera are examined for PRP Ab at 3 weeks after the initial injection. The radioimmunoassay (RIA) method used for the measurement of PRP Ab is described by Kuo, J. S. -C., Monji, N., Schwalbe, R. S. and McCoy, D. W. "A Radioactive Antigen-Binding Assay For The Measurement of Antibody to *Haemophilus Influenzae* Type b Capsular Polysaccharide" in the Journal of Immunological Methods 43 35-47 (1981) which is incorporated by reference.

Rats injected with PRP alone, prepared by the above procedure, show PRP antibody titer of about 22 ng/ml. The age and the strain of the rats injected with PRP alone is similar to the rats injected with the above combined vaccine.

EXAMPLE 2

A 0.3 ml of PRP solution (1 mg/ml PBS), and 1.5 ml (1 mg protein/ml PBS) of *B. pertussis* outer membrane prepared by the lysozyme treatment method are added to 13.2 ml of PBS containing 0.01% thimerosal to make a vaccine solution containing 10 μg PRP and 50 μg protein per dose (0.5 ml).

The combined vaccine (0.5 ml dose) is then injected into young rats; they are injected once a week for three weeks. The age and the strain of each rat is similar.

The results of the antibody response to vaccines 1,2 and 3 prepared at three different times by the above procedure are as follows:

| | | PRP Antibody Level (ng/ml) | | | |
|---|---|---|---|---|---|
| Rat # | Vaccine 1 | Rat # | Vaccine 2 | Rat # | Vaccine 3 |
| 1 | 440 | 5 | 144 | 9 | 556 |
| 2 | 200 | 6 | 132 | 10 | 880 |
| 3 | 608 | 7 | 312 | 11 | 960 |
| 4 | 180 | 8 | 556 | 12 | 164 |

PRP antibody levels are measured by RIA at 4 weeks after the initial injection. The RIA method used is described in Example 1.

Rats injected with PRP alone, prepared by the procedure of Example 1, show PRP antibody titer of about 22 ng/ml. The age and the strain of the rats injected with PRP alone is similar to the rats injected with the above combined vaccine.

EXAMPLE 3

A 0.3 ml PRP solution (1 mg/ml PBS), and 1.5 ml (0.8 mg protein/ml PBS) of *B. pertussis* outer membrane peak II isolated by the LiCl-LiAc method are added to 13.2 ml of PBS containing 0.01% thimerosal to make a vaccine solution containing 10 μg PRP and 40 μg protein per dose (0.5 ml).

The combined vaccine (0.5 ml per dose) is then injected into young rats; they are injected once a week for three weeks. The age and the strain of each rat is similar.

The results of the antibody response to vaccines 1, 2 and 3 prepared at three different times by the above procedure are as follows:

| Rat # | Vaccine 1 | Rat # | Vaccine 2 | Rat # | Vaccine 3 |
|---|---|---|---|---|---|
| 1 | 792 | 5 | 124 | 9 | 340 |
| 2 | 144 | 6 | 188 | 10 | 76 |
| 3 | 236 | 7 | 60 | 11 | 276 |
| 4 | 776 | 8 | 436 | 12 | 780 |

PRP antibody levels are measured by RIA at 4 weeks after the initial injection. The radioimmunoassay method used is described in Example 1.

Rats injected with PRP alone, prepared by the procedure of Example 1, show PRP antibody titer of about 22 ng/ml. The age and the strain of the rats injected with PRP alone is similar to the rats injected with the above combined vaccine.

We claim:

1. A combined vaccine for eliciting polyribosyl ribitol phosphate (PRP) antibody formations in warm-blooded animals comprising the capsular polysaccharide PRP isolated and purified from *Haemophilus influenzae* type b and antigens isolated and purified from an outer membrane component of *Bordetella pertussis*.

2. A combined vaccine of claim 1 wherein said PRP is obtained from *H. influenzae* type b CK strain.

3. A combined vaccine of claim 1 wherein said PRP is obtained from *H. influenzae* type b Rab strain.

4. A combined vaccine of claim 1 or 2 or 3 wherein said *B. pertussis* antigens are obtained from *Bordetella pertussis* strain 138.

5. A combined vaccine according to claim 4 wherein said warm-blooded animal is a human child.

6. A method for inducing active immunization in warm-blooded animals against systemic infection caused by the pathogen *H. influenzae* type b comprising administering an immunogenic amount of a combined vaccine comprising the capsular polysaccharide PRP isolated and purified from *H. influenzae* type b and antigens isolated and purified from an outer membrane component of *B. pertussis*.

7. A method of claim 6 wherein said warm-blooded infection is meningitis.

* * * * *